(12) United States Patent
Van Breugel

(10) Patent No.: US 8,664,435 B2
(45) Date of Patent: Mar. 4, 2014

(54) LIQUID LACTIC ACID COMPOSITION AND METHOD FOR PREPARATION THEREOF

(75) Inventor: Jan Van Breugel, Woudrichem (NL)

(73) Assignee: Purac Biochem B.V., Gorinchem (NL)

( * ) Notice: Subject to any disclaimer, the term of this patent is extended or adjusted under 35 U.S.C. 154(b) by 111 days.

(21) Appl. No.: 13/384,297

(22) PCT Filed: Jul. 15, 2010

(86) PCT No.: PCT/EP2010/060218
§ 371 (c)(1),
(2), (4) Date: Mar. 9, 2012

(87) PCT Pub. No.: WO2011/006965
PCT Pub. Date: Jan. 20, 2011

(65) Prior Publication Data
US 2012/0165568 A1   Jun. 28, 2012

(30) Foreign Application Priority Data
Jul. 16, 2009  (EP) .................................. 09165616

(51) Int. Cl.
*C07C 51/42* (2006.01)
*C07C 51/43* (2006.01)
*C07C 59/08* (2006.01)

(52) U.S. Cl.
USPC ........................................ 562/580; 562/589

(58) Field of Classification Search
USPC ................................. 562/580, 589
See application file for complete search history.

(56) References Cited

U.S. PATENT DOCUMENTS

| | | | |
|---|---|---|---|
| 6,630,603 B1 | 10/2003 | Van Breugel | |
| 6,632,966 B2 * | 10/2003 | Gerkema et al. | 562/589 |
| 6,747,173 B2 * | 6/2004 | Gerkema et al. | 562/589 |
| 7,002,039 B2 * | 2/2006 | van Krieken | 562/580 |
| 7,223,885 B2 * | 5/2007 | van Krieken | 562/580 |
| 2004/0116740 A1 | 6/2004 | Van Krieken | |

FOREIGN PATENT DOCUMENTS

| | | |
|---|---|---|
| CN | 1344241 A | 4/2002 |
| CN | 1474799 A | 2/2004 |
| WO | WO 98/55442 | 12/1998 |
| WO | WO 00/56693 | 9/2000 |
| WO | WO 0138283 | 5/2001 |

OTHER PUBLICATIONS

Database CAPLUS on STN, Acc. No. 1960:64565, SEVAST'YANOVA, Za Industrial'nuyu Ryazan. Byull. Tekh.-Ekon. Inform. (1958), No. 4, p. 16-17 (abstract).*
European Search Report and the Written Opinion of the European Patent Office Patent Office in counterpart foreign application No. PCT/EP2010/060218 filed Jul. 15, 2010.
Chinese Office Action. Application No. 201080038762.0. Oct. 10, 2013.

* cited by examiner

*Primary Examiner* — Brian J Davis
(74) *Attorney, Agent, or Firm* — Peter J. Ims; Westman, Champlin & Koehler P.A.

(57) ABSTRACT

A method of preparing a liquid lactic acid composition that has a total acid content of at least 94% (w/w) and that does not crystallize at a temperature above 10° C. includes obtaining a starting liquid lactic acid composition that has a total acid content of at least 94% (w/w) and that crystallizes at a temperature above 10° C. and incubating said starting liquid lactic acid composition at a temperature above the crystallization point of the starting liquid lactic acid composition for a time period to obtain the liquid lactic acid composition that does not crystallize at a temperature above 10° C.

23 Claims, No Drawings

LIQUID LACTIC ACID COMPOSITION AND METHOD FOR PREPARATION THEREOF

CROSS-REFERENCE TO RELATED APPLICATION

This Application is a Section 371 National Stage Application of International Application No. PCT/EP2010/060218, filed Jul. 15, 2010 and published as WO 2011/006965 A1 on Jan. 20, 2011, in English, which in turn is based on and claims benefit of U.S. Provisional Application No. 61/213,801 filed Jul. 16, 2009.

BACKGROUND

The discussion below is merely provided for general background information and is not intended to be used as an aid in determining the scope of the claimed subject matter.

An aspect of the present invention relates to a method for the preparation of a highly concentrated liquid lactic acid composition and a composition obtainable by said method.

Lactic acid as well as its salts and esters have long been used as food additive and in various chemical and pharmaceutical applications. More recently, lactic acid has been used in the making of biodegradable polymers both as a replacement for present plastic materials as well as various new uses where biodegradability is needed or desired such as for medical implants and slow release drugs. Accordingly there is an ever-increasing demand for improved and economically viable lactic acid production processes.

Lactic acid is commonly marketed as a dilute or concentrated aqueous solution, whereby concentrated lactic acid solutions generally have a lactic acid concentration of about 90% (w/w). The marketing of lactic acid compositions having even higher concentrations is still desirable, e.g. to decrease packaging and transport costs and to improve ease of use in all kinds of technical and food applications. However, higher concentrations are not feasible because crystallisation of lactic acid in such highly concentrated compositions easily occurs at an ambient temperature, which provides problems with handling the lactic acid composition.

It is desirable to provide a highly concentrated liquid lactic acid composition that does not crystallise at an ambient temperature.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

A method for the preparation of a liquid lactic acid composition includes the preparation of a liquid lactic acid composition that has a total acid content of at least 94% (w/w) and that does not crystallise at a temperature above 10° C. The method comprises obtaining a starting liquid lactic acid composition that has a total acid content of at least 94% (w/w) and that crystallises at a temperature above 10° C., and incubating said starting liquid lactic acid composition at an elevated temperature, i.e. at a temperature above the crystallisation point of the starting liquid lactic acid composition, for a suitable time period to obtain a liquid lactic acid composition that does not crystallise at a temperature above 10° C.

DETAILED DESCRIPTION

The liquid lactic acid composition obtained by the method as described herein is a liquid ready-to-use composition suitable to be packed and put into the market.

Preferably, the liquid lactic acid composition that does not crystallise at a temperature above 10° C. has a total acid content of at least 95% (w/w), more preferably at least 96%, 97%, 98%, 99% (w/w). Especially preferable, the liquid lactic acid composition that does not crystallise at a temperature above 10° C. has a total acid content of 100% (w/w). In addition, a liquid lactic acid composition with a total acid content of higher than 100% (w/w) may be obtained by removing part or all of the water that is present in the liquid lactic acid composition being subjected to the incubation at an elevated temperature as described herein. Such water my suitably be removed by evaporation. It is noted that the presence of water in such a liquid lactic acid composition is partly or wholly (in a liquid composition having a total acid content of 100% (w/w)) due to the incubation at an elevated temperature.

It was surprisingly found that a liquid lactic acid composition that has a high total acid content of at least 94% (w/w) and that does not crystallise at a temperature above 10° C. is obtained from a starting lactic acid composition that has the same total acid content as the liquid "end" composition but that does crystallise at a temperature above 10° C., by incubating the starting lactic acid composition for a prolonged time period at an elevated temperature above the crystallisation point of the starting liquid lactic acid composition.

It was also found that the resulting liquid lactic acid composition having a total acid content of at least 94% (w/w) has a ratio total acid/free acid of 1.2-1.7, preferably of 1.2-1.4.

The total acid content (TA) of a composition is the monomeric acid content measured after complete hydrolysis of any intermolecular ester bond with a precisely known amount of excess base and determined by back titration of remaining base with acid. The total acid content thus gives the content of monomeric and oligomeric lactic acid and is expressed as the percentage (w/w) of monomeric lactic acid. Oligomeric lactic acid typically comprises dimeric (HL2), trimeric (HL3), tetrameric (HL4) and pentameric acid (HL5), and a small amount of dilactide (L2).

The free acid content (FA) of a composition is determined by direct titration with base, i.e. without hydrolysis of the intermolecular ester bonds.

The starting liquid lactic acid composition is a composition that crystallises at a temperature above 10° C. and below its crystallisation point. The crystallisation point will depend on the concentration of the starting liquid lactic acid composition. For instance, the crystallisation point of a 94% (w/w) lactic acid composition is 37° C. and that of 100% lactic acid is 53° C. Typically, the starting liquid lactic acid composition crystallises at an ambient temperature, for instance a temperature between 15° C. and 25° C. Such a starting composition can be obtained in various ways.

The starting composition may for instance be obtained by concentrating a solution of lactic acid, for instance a commercial solution, until the total acid content is 94% or higher. Concentration of a lactic acid solution may be done by evaporating a dilute lactic acid solution, by treatments in which use is made of membranes or molecular sieves and/or by distillation under reduced pressure.

The starting composition may also be obtained by stirring solid lactic acid in an appropriate amount of solvent and heating the mixture until being liquid.

The starting composition may also be obtained immediately after a suitable process step in a process for the preparation of lactic acid. Suitable processes for the preparation of lactic acid for instance are disclosed in WO 98/55442 and WO 01/38283, which are incorporated herein by reference. In that regard, an especially suitable process step is the distillation step as described herein below.

Lactic acid is commonly produced by fermentation by means of a micro-organism, such as bacteria, yeasts and fungi. The fermentation substrate typically comprises carbohydrates, such as glucose, sucrose, starch, and the like, together with suitable minerals and nitrogen-containing nutrients. Known microorganisms producing S-lactic acid are various bacteria of the genus *Lactobacillus*, such as *Lactobacillus casei*, or *Bacillus*, such as *Bacillus coagulans*. In addition microorganisms are known which produce (R)-lactic acid selectively.

After fermentation, the aqueous fermentation broth is processed in order to obtain lactic acid having a purity as desired. The usual industrial processing path generally consists of separation of the biomass followed by one or more additional processing steps.

Usually, the biomass is separated by means of filtration, centrifugation, flocculation, coagulation, flotation or combinations thereof. This is for instance described in WO 01/38283 wherein a continuous process for the preparation of lactic acid by means of fermentation is described.

The fermentation liquid is further processed as necessary to obtain a lactic acid solution having a purity as desired. These process steps may include well known process steps, such as ion exchange, distillation, crystallisation, melting, esterification, water evaporation, saponification, acidulation, filtration, extraction, adsorption.

It is preferred for the lactic acid solution to be distilled under reduced pressure to obtain the starting lactic acid composition that is to be subjected to the incubation at an elevated temperature as described herein. Reduced pressure is to be understood as a pressure in a range of from 0.01 to 100 mbar, preferably from 0.1 to 20 mbar, in particular from 1 to 10 mbar. The temperature during the distillation under reduced pressure may be from 100 to 200° C., in particular from 110 to 140° C.

The distillation may be carried out as follows, and repeated one or more times as desired, for instance as described in WO 01/38283, which was previously incorporated herein by reference.

Briefly, in a first step, the aqueous lactic acid solution is brought into the vapour phase by, for instance, film evaporation. Film evaporation can be achieved by means of lubricated film evaporation, thin-film evaporation and/or falling-film evaporation. Then, the vapour is passed onto a distillation column, in which separation into two fractions occurs under reflux conditions. The distillation column may have a number of trays of from 1 to 10. The distillation under reduced pressure results in the removal of impurities having a higher boiling point than lactic acid, as the lactic acid is obtained as the top product. The top product contains at least 94% (w/w) of total acid, and the residue contains residual sugars and/or polymeric lactic acid.

In the case of a lactic acid solution, the solvent is preferably water, although other solvents such as C1-C5 alkanols (methanol, ethanol, 1-propanol, 2-propanol, 1-butanol, 2-butanol, 2-methyl-1-propanol, 2-methyl-2-propanol, 1-pentanol, 2-pentanol, 3-pentanol, 2-methyl-1-butanol, 2-methyl-2-butanol, 3-methyl-1-butanol, 3-methyl-2-butanol and 2,2-dimethylpropanol) are also suitable or may be mixed with water.

The starting lactic acid composition having a total acid content of at least 94% (w/w) is brought to an elevated temperature, i.e. a temperature above its crystallisation point, and incubated at said temperature for a suitable time period to obtain a liquid lactic acid composition that does not crystallise at a temperature above 10° C. The upper limit for the incubation temperature suitably may be the boiling point of the lactic acid composition at the pressure concerned. The incubation may be done under agitation using any agitation device known to the person skilled in the art.

Preferably, the incubation temperature is in a range of 40° to 120° C., more preferably in a range of 50° to 100° C., most preferably in a range of 60° to 90° C. The time period for incubation typically will depend on the applied temperature or temperature range. The higher the incubation temperature, the shorter the incubation period. For instance, at a temperature of 100° C. the incubation period may be about 1-4 hours, at a temperature of 80° C. the incubation period may be about 3-12 hours, and at a temperature of about 60° C. the incubation period may be about 10-40 hours. Thus, the incubation period may be at least about 30 minutes, preferably at least about 1 hour, more preferably at least about 2 hours, most preferably at least about 3 hours. The incubation may be performed at a fixed temperature or using a temperature range, and may include the period for cooling down to ambient temperature.

The skilled person will understand that the incubation may be ended at such a point in time where a liquid lactic acid composition is obtained which, upon cooling of the composition to a temperature of 10° C., is still liquid and does not contain crystals. Such a point in time may suitably be determined by taking a sample of 50 ml, bringing this sample to a temperature of 10° C. and adding 1 g of lactic acid seed crystals under stirring. If the seed crystals dissolves in about 1 hour under stirring, the liquid lactic acid composition does not crystallise at a temperature above 10° C. and the incubation may be ended.

The incubation of the starting lactic acid composition at an elevated temperature above its crystallisation point as described herein may advantageously encompass a previous and/or further processing step, provided that said processing step is carried out at the elevated temperature. For instance, a further processing step may be the removal of remaining impurities such as colouring substances. This removal may be done by passing the liquid lactic acid composition over a carbon column. The time period of said passing, for instance 3 hours, may be included in the incubation time period as mentioned above.

An aspect of the present invention is applicable to compositions comprising lactic acid in any stereochemical configuration, i.e. $L^+$- or $D^-$-lactic acid or any mixture of $L^+$- and $D^-$-lactic acid.

In a further aspect, a liquid lactic acid composition is provided that has a total acid content of at least 94% (w/w) and that does not crystallise at a temperature above 10° C. Preferably, the liquid lactic acid composition that does not crystallise at a temperature above 10° C. has a total acid content of at least 95% (w/w), more preferably at least 96%, 97%, 98%, 99% (w/w). Especially preferable, the liquid lactic acid composition that does not crystallise at a temperature above 10° C. has a total acid content of 100% (w/w).

The liquid lactic acid composition having a total acid content of at least 94% (w/w) further preferably has a ratio total acid/free acid in a range from about 1.2 to about 1.7, preferably in a range from about 1.2 to about 1.4. In particular, the liquid lactic acid composition may have a content of monomeric (HL1) plus dimeric (HL2) lactic acid in a range from about 65% to about 85% (w/w), preferably in a range from about 75% to about 84% (w/w), and/or may have a content of monomeric (HL1) plus dimeric (HL2) plus trimeric (HL3) lactic acid in a range from about 80% to about 91% (w/w), preferably in a range from about 87% to about 90% (w/w).

Such liquid lactic acid compositions may have a composition as specified herein below (at a temperature of 25° C.). The composition conveniently may be determined using mass spectroscopy.

| | Composition (% w/w) | | | | |
|---|---|---|---|---|---|
| TA | 94 | 96 | 98 | 100 | 105 |
| FA | 75.8 | 75.1 | 73.8 | 72.1 | 64.9 |
| TA/FA | 1.24 | 1.28 | 1.33 | 1.39 | 1.62 |
| HL1 | 61.3 | 58.8 | 55.7 | 51.9 | 39.6 |
| HL2 | 21.2 | 23.0 | 24.7 | 26.3 | 28.2 |
| HL3 | 5.9 | 7.2 | 8.8 | 10.7 | 16.1 |
| HL4 | 1.5 | 2.1 | 2.8 | 3.9 | 8.3 |
| HL5 | 0.4 | 0.6 | 0.9 | 1.4 | 4.1 |
| L2 | 0.2 | 0.2 | 0.3 | 0.3 | 0.7 |
| Water | 9.6 | 8.2 | 6.8 | 5.6 | 3.0 |

The composition of this aspect is preferably obtainable by the method according to the previous aspect.

The highly concentrated liquid lactic acid composition as disclosed herein may advantageously be used in any lactic acid application. The liquid form combined with the high acid concentration provides advantages like ease of handling and the lowest possible transport costs.

The invention claimed is:

1. A method to prepare a liquid lactic acid composition that has a total acid content of at least 94% (w/w) and that does not crystallise at a temperature above 10° C., the method comprising obtaining a starting liquid lactic acid composition that has a total acid content of at least 94% (w/w) and that crystallises at a temperature above 10° C. and incubating said starting liquid lactic acid composition at a temperature above the crystallisation point of the starting liquid lactic acid composition for a time period to obtain the liquid lactic acid composition that does not crystallise at a temperature above 10° C.

2. The method according to claim 1 further comprising removing part of the water that is present in the liquid lactic acid composition obtained after the incubation at a temperature above the crystallisation point of the starting liquid lactic acid composition.

3. The method according to claim 1, wherein the incubation temperature is in a range of 40° C. to 120° C.

4. The method according to claim 1, wherein the incubation period is at least about 30 minutes.

5. The method according to claim 1, wherein the starting lactic acid composition is distilled prior to being incubated.

6. The method according to claim 1, and further comprising a further processing step at a temperature above the crystallisation point of the starting liquid lactic acid composition, wherein the further processing step comprises passing the liquid lactic acid composition through a carbon column to remove coloring substances.

7. A liquid lactic acid composition that has a total acid content of at least 94% (w/w) and that does not crystallise at a temperature above 10° C.

8. The liquid lactic acid composition of claim 7 having a total acid content of at least 95% (w/w).

9. The liquid lactic acid composition of claim 7 having a total acid content of 100% (w/w).

10. The liquid lactic acid composition of claim 7 having a ratio total acid/free acid in a range from about 1.2 to about 1.7.

11. A liquid lactic acid composition prepared by the process comprising the steps of obtaining a starting liquid lactic acid composition that has a total acid content of at least 94% (w/w) and that crystallises at a temperature above 10° C. and incubating said starting liquid lactic acid composition at a temperature above the crystallisation point of the starting liquid lactic acid composition for a time period to obtain the liquid lactic acid composition of at least 94% (w/w) that does not crystallise at a temperature above 10° C.

12. The liquid lactic acid composition of claim 11 and wherein the time period for incubating the starting liquid lactic acid composition comprises at least 30 minutes.

13. The liquid lactic acid composition of claim 11 and wherein the incubation temperature is in a range of 40° C. to 120° C.

14. The liquid lactic acid composition of claim 11 wherein the process further comprises the step of removing part of the water that is present in the liquid lactic acid composition obtained after the incubation at a temperature above the crystallisation point of the starting liquid lactic acid composition.

15. The liquid lactic acid composition of claim 11 wherein the process further comprises the step of removing all of the water that is present in the liquid lactic acid composition obtained after the incubation at a temperature above the crystallisation point of the starting liquid lactic acid composition.

16. The liquid lactic acid composition of claim 11 wherein the process further comprises a further processing step at a temperature above the crystallisation point of the starting liquid lactic acid composition, wherein the further processing step comprises passing the liquid lactic acid composition through a carbon column to remove coloring substances.

17. The method according to claim 1 further comprising removing all of the water that is present in the liquid lactic acid composition obtained after the incubation at a temperature above the crystallisation point of the starting liquid lactic acid composition.

18. The method according to claim 1, wherein the incubation period is at least about 3 hours.

19. The liquid lactic acid composition of claim 7 having a total acid content of at least 96% (w/w).

20. The liquid lactic acid composition of claim 7 having a total acid content of at least 97% (w/w).

21. The liquid lactic acid composition of claim 7 having a total acid content of at least 98% (w/w).

22. The liquid lactic acid composition of claim 7 having a total acid content of at least 99% (w/w).

23. The liquid lactic acid composition of claim 7 having a ratio total acid free acid in a range from about 1.2 to about 1.4.

* * * * *

UNITED STATES PATENT AND TRADEMARK OFFICE
CERTIFICATE OF CORRECTION

PATENT NO. : 8,664,435 B2  
APPLICATION NO. : 13/384297  
DATED : March 4, 2014  
INVENTOR(S) : Jan Van Breugel Page 1 of 1

It is certified that error appears in the above-identified patent and that said Letters Patent is hereby corrected as shown below:

On the Title Page

In the References Cited item 56:

For European Search Report publication citation, delete "Patent Office Patent Office" and insert --Patent Office--

In the Claims

In Claim 23, col. 6, line 59, delete "total acid free acid" and insert --total acid / free acid--

Signed and Sealed this
Eighteenth Day of August, 2015

Michelle K. Lee  
*Director of the United States Patent and Trademark Office*

UNITED STATES PATENT AND TRADEMARK OFFICE
CERTIFICATE OF CORRECTION

PATENT NO. : 8,664,435 B2  
APPLICATION NO. : 13/384297  
DATED : March 4, 2014  
INVENTOR(S) : Jan Van Breugel Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 164 days.

Signed and Sealed this

Twenty-ninth Day of September, 2015

Michelle K. Lee
*Director of the United States Patent and Trademark Office*